United States Patent [19]

Matsuoka et al.

[11] Patent Number: 5,911,908
[45] Date of Patent: Jun. 15, 1999

[54] METHOD OF STABILIZING 4,6-DIAMINORESORCINOL AND SALT THEREOF

[75] Inventors: Go Matsuoka; Fuyuhiko Kubota, both of Ohtsu, Japan

[73] Assignee: Toyo Boseki Kabushiki Kaisha, Osaka, Japan

[21] Appl. No.: 09/095,366

[22] Filed: Jun. 10, 1998

[51] Int. Cl.⁶ ..................................................... C09K 3/00
[52] U.S. Cl. ........................ 252/182.29; 564/418; 564/423
[58] Field of Search ........................ 252/182.29; 564/418, 564/423

[56] References Cited

U.S. PATENT DOCUMENTS

| | | | |
|---|---|---|---|
| 5,001,279 | 3/1991 | Yin et al. | 568/709 |
| 5,414,130 | 5/1995 | Lysenko et al. | 564/418 |

FOREIGN PATENT DOCUMENTS

| | | |
|---|---|---|
| 0 266 222 | 5/1988 | European Pat. Off. . |
| 0 312 931 | 4/1989 | European Pat. Off. . |
| WO 93 08156 | 4/1993 | WIPO . |

OTHER PUBLICATIONS

Database WPI, Section Ch, Week 8603, Derwent Publications Ltd., London, GB; Class E14, AN 86–017023 XP–002074568 & JP 60 239 447 abstract (1986).

*Primary Examiner*—Brian M. Burn
*Attorney, Agent, or Firm*—Morrison & Foerster

[57] ABSTRACT

A method for stabilizing DAR during storage, comprising storing DAR in the presence of a reducing agent having a standard redox potential of not less than −0.20 volt and not more than 0.34 volt, in a proportion of not less than 100 ppm and not more than 10,000 ppm of DAR. The present invention improves storage stability of DAR. This in turn results in easy handling and long-term preservation of DAR. Thus, a high quality polymer PBO can be easily produced and the invention greatly contributes to the industrial field.

3 Claims, No Drawings

METHOD OF STABILIZING 4,6-DIAMINORESORCINOL AND SALT THEREOF

TECHNICAL FIELD OF THE INVENTION

The present invention relates to 4,6-diaminoresorcinol having superior storage stability and a salt thereof (hereinafter generally referred to as DAR). The present invention also relates to a method of stabilizing DAR.

BACKGROUND OF THE INVENTION

DAR has been conventionally known as a starting material of polybenzbisoxazole (hereinafter to be referred to as PBO) which can be processed into a highly strong fiber having a high elastic modulus. PBO is synthesized by various methods inclusive of a method using resorcinol as a starting material, as described in Japanese Patent Unexamined Publication Nos. 242604/1995, 136/1990, U.S. Pat. Nos. 5,410,083 and 5,453,542, a method using trichlorobenzene as a starting material, as described in Japanese Patent Application under PCT laid-open under kohyo Nos. 500743/1990 and 502028/1993 and a method using m-dichlorobenzene as a starting material, as described in Japanese Patent Unexamined Publication Nos. 238561/1989 and 24038/1991. Industrialization of DAR has been desired.

On the other hand, DAR has a shortcoming that it is susceptible to oxidation. When left in atmosphere, for example, it is discolored due to oxidation in several days, or several hours when the oxidation proceeds faster. When PBO is obtained by polymerizing such DAR as a starting material, only a polymer discolored to green to purple and having a low polymerization degree is obtained. This in turn requires an inert atmosphere for the storage and handling of DAR, as well as complete drying of DAR. Even under such environment, degradation due to oxidation is inevitable by a long-term storage over several months. Therefore, a formed product (e.g., fiber and film) of PBO having superior property and quality has been unattainable by prior art techniques.

Japanese Patent Examined Publication No. 21166/1994 proposes addition of a reducing oxide of phosphorus or sulfur during polymerization to give a high quality PBO. The addition aims at suppressing DAR's decomposition during polymerization, and does not overcome poor storage stability of DAR.

Likewise, U.S. Pat. No. 5,142,021 proposes addition of tin chloride during polymerization for the same purpose as in Japanese Patent Examined Publication No. 21166/1994.

Japanese Patent Unexamined Publication No. 136/1990 teaches addition of tin chloride during production of DAR in an example. One of the purposes of the addition is to use it as a hydrogenating agent of reactive intermediate, nitro-1,3-benzenediol. The other purpose is to reduce impurity with tin chloride during purification by recrystallization. Thus, tin chloride is not present during the storage of DAR, and the addition does not overcome poor storage stability of DAR.

As mentioned above, synthetic methods of DAR have been actively studied and many techniques have been proposed. However, a stabilizing technique of DAR has not been found and industrial production of DAR has not been realized. It is therefore an object of the present invention to provide DAR having an improved storage stability.

The present invention further aims at providing a stabilizing method of DAR during storage.

SUMMARY OF THE INVENTION

The present invention now provides a DAR having a noticeably improved storage stability that is obtained by adding a certain reducing agent.

Thus, the present invention provides the following:
(1) A composition consisting essentially of 4,6-diaminoresorcinol or a salt thereof, and a reducing agent having a standard redox potential of not less than −0.20 volt and not more than 0.34 volt, in a proportion of not less than 100 ppm and not more than 10,000 ppm of DAR.
(2) A method for producing polybenzbisoxazole, comprising reacting 4,6-diaminoresorcinol with an aromatic dicarboxylic acid in the presence of a reducing agent having a standard redox potential of not less than −0.20 volt and not more than 0.34 volt in a proportion of not less than 100 ppm and not more than 10,000 ppm of DAR.
(3) A method for stabilizing 4,6-diaminoresorcinol or a salt thereof during storage, comprising storing 4,6-diaminoresorcinol or salt thereof in the presence of a reducing agent having a standard redox potential of not less than −0.20 volt and not more than 0.34 volt, in a proportion of not less than 100 ppm and not more than 10,000 ppm of DAR.

DETAILED DESCRIPTION OF THE INVENTION

The present invention is explained in more detail in the following.

In the present invention, DAR can be obtained by a conventional method. For example, the methods described in Japanese Patent Application under PCT laid-open under kohyo No. 500743/1990, Japanese Patent Unexamined Publication Nos. 242604/1995 and 136/1990, U.S. Pat. Nos. 5,410,083 and 5,453,542, Japanese Patent Application under PCT laid-open under kohyo No. 502028/1993, Japanese Patent Unexamined Publication Nos. 238561/1989 and 24038/1991, and the like can be used.

The DAR obtained by the above-mentioned method is generally used in the form of a dihydrochloride. In the present invention, DAR is not limited to dihydrochloride, but may be inorganic acid salt such as disulfate and diphosphate or organic acid salt such as terephthalate and diacetate.

The reducing agent in the present invention is a compound having a standard redox potential of not less than −0.20 volt and not more than 0.34 volt, preferably not less than 0.0 volt and not more than 0.20 volt. PBO is polymerized upon dissolution of DAR and terephthalic acid in polyphosphoric acid. The reducing agent having a standard redox potential of less than −0.20 volt undesirably causes generation of hydrogen upon reaction with phosphoric acid when DAR is dissolved in polyphosphoric acid during the production of PBO. When the standard redox potential exceeds 0.34 volt, DAR is not stabilized.

Examples of the reducing agent in the present invention include metal salts such as $TiCl_3$, $CuCl$, $SnCl_2$ and the like, reducing oxide of phosphorus or sulfur, such as hypophosphorous acid and sodium thiosulfate and the like. Of these, metal chloride such as TiCl$_3$, CuCl and SnCl$_2$ are particularly preferable in view of a great effect achieved for a little amount thereof. In particular, SnCl$_2$ and hydrate thereof are colorless and most preferable.

In the present invention, the amount of a reducing agent varies depending on its kind. It is essential that the reducing agent be constantly contained in at least not less than 100 ppm, preferably not less than 1,000 ppm and more preferably not less than 2,000 ppm, of DAR or its salt during the storage of DAR. When it is less than 100 ppm, DAR cannot be stabilized sufficiently. The stabilizing effect of that level would not cause any problem for a short-term storage or use, but is not sufficient when it is preserved for a long term such as several months. When it is contained in 10,000 ppm, the stabilizing effect is sufficient. Its content greater than that only results in higher costs and unwanted effects such as a great amount of a reducing agent as a contaminant in waste solvents during PBO production. The reducing agent is preferably added during production of DAR, for example, during precipitation or drying. It is added in a molten state or upon dissolution in a volatile solution. Addition in a solid state prevents uniform mixing with DAR and possibly induces local progression of decomposition. The obtained DAR preferably carries the reducing agent uniformly attached to the surface of the DAR crystals.

The DAR of the present invention having the above-mentioned construction can be used particularly as a starting material of PBO. This PBO obtained using DAR and an aromatic dicarboxylic acid is homopolymer or copolymer having structural units of the following formula (I).

It has been found that when the above-mentioned PBO is produced by polymerization of the above-mentioned DAR, a polymer having a high polymerization degree and fine color can be obtained, even after leaving the inventive DAR in contact with the air for more than 3 months.

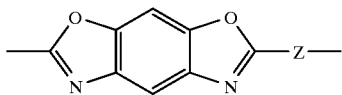
(I)

wherein Z is a divalent aromatic organic residue which is represented by the following formulas (II) to (V).

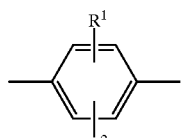
(II)

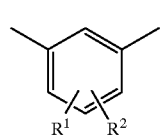
(III)

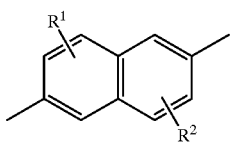
(IV)

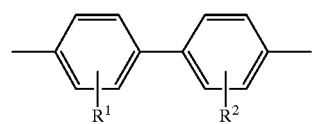
(V)

wherein, in the formulas (II) to (V), R$^1$ and R$^2$ may be the same or different and each is H, OH, alkyl having 1 to 4 carbon atoms, OR$^3$ wherein R$^3$ is alkyl having 1 to 4 carbon atoms, or halogen atom.

A method for forming PBO into a fiber has been proposed in a number of patents. The PBO obtained using DAR of the present invention can be produced by a method known per se, such as a method disclosed in U.S. Pat. Nos. 5296185 and 5294390. A film can be also produced by a method known per se.

One preferable embodiment of the present invention is shown in the following, to which the present invention is not limited. 4,6-Diaminoresorcinol dihydrochloride is synthesized according to the method disclosed in Japanese Patent Application under PCT laid-open under kohyo No. 500743/1990. As a reducing agent, a solution of tin (II) chloride or its hydrate in hydrochloric acid is uniformly sprayed on DAR. Then, the mixture is dried in vacuo by heating and stirring in a dryer at 40° C. –100° C. to give DAR containing tin (II) chloride in 100–10,000 ppm. It is possible to use the resulting DAR at once for the next step. For assessment of storage stability, it is preserved in contact with atmosphere for 2 months at 30° C., and PBO is produced by polymerization.

For polymerization of PBO, the amounts of the starting materials are adjusted to achieve a polymer concentration of 5–20% by weight. 4,6-Diaminoresorcinol dihydrochloride obtained above, finely-divided terephthalic acid, polyphosphoric acid (105–120%) and phosphorus pentaoxide are heated and mixed at 70–220° C. by, for example, the method described in U.S. Pat. No. 4,533,693 to Wolfe. As a result, a polymer having a high polymerization degree in a yellow dope can be obtained.

The polymer thus obtained is fed into a spinning part and delivered from a spinneret generally at a temperature of not less than 100° C. The delivered dope (yarn before extraction of polyphosphoric acid) is taken up by a stress isolator such as godet rolls at a constant speed and drawn in a non-coagulant gas. The dope filaments solidified by cooling after yarn delivery is led to a coagulation bath containing an aqueous or alcohol solution. The yarn passed through the coagulation bath passes godet rolls. Finally, it is washed in an extraction bath containing water, methanol and the like until the concentration of phosphoric acid in the yarn becomes not more than 1.0%, preferably not more than 0.5%. A bundle of said fibers is neutralized with an aqueous solution of sodium hydroxide and further washed with water. After such treatment, it is dried in a dryer using high temperature air. The single fiber constituting the fiber bundle thus obtained has a sufficient strength of not less than 35 g/d and a sufficient elastic modulus of not less than about 1000 g/d.

The present invention is further explained in more detail by way of the following Examples, to which the present invention is not limited. In the Examples, DAR was dissolved in 1N aqueous hydrochloric acid solution and UV spectrum was measured, and the decomposition degree of DAR was calculated from the absorbance at 320 nm which was derived from decomposition product of DAR. The intrinsic viscosity of PBO was measured at 25° C. using methanesulfonic acid as a solvent. EXAMPLE 1

Application of Reducing Agent

Tin (II) chloride (4.0 g) was dissolved in 20 ml of aqueous hydrochloric acid solution to give a 2 mol/l tin chloride solution.

This solution was uniformly sprayed on 4,6-diaminoresorcinol dihydrochloride (1000 g) obtained by the method described in Japanese Patent Application under PCT laid-open under kohyo No. 500743/1990. Then, it was dried under reduced pressure while stirring in a rotary evaporator. The temperature was maintained from 40° C. to 100° C. during drying. After drying, divalent Sn in DAR was measured using a polarography (device used: 693VA Processor, 694VA Stand, 685 Dosimat, available from Metrom) and found to be 1800 ppm, 2880 ppm when converted to $SnCl_2$. This DAR was preserved for 3 months at 30° C. in contact with the air, and its decomposition degree was measured and found to be 0.0%.

EXAMPLE 2

Polymerization to give PBO

Polyparap henylene benzbisoxazole (PBO) was polymerized using DAR obtained in Example 1. To be specific, diphosphorus pentaoxide (14.49 kg) was added to 116% polyphosphoric acid (43.86 kg) under a nitrogen atmosphere. Then, 4,6-diaminoresorcinol dihydrochloride (9.10 kg) obtained in Example 1 and terephthalic acid (7.10 kg) finely divided to an average particle size of 2 μm were added, and the mixture was stirred and mixed in a reactor tank at 80° C. It was further heated and mixed at 150° C. for 10 hours and polymerized in a twin-screw extruder heated to 200° C. to give a polymer dope of cis-polyparaphenylene benzbisoxazole. The polymer dope was yellow and had an intrinsic viscosity of 38 dl/g.

EXAMPLE 3

Manufacture of Fiber

The dope obtained in Example 2 was sent from the extruder to a gear pump while maintaining its temperature at 170° C. The dope was spun from a spinneret having 668 holes at 170° C. The delivered yarn was cooled with cooling air at 60° C., brought into contact with aqueous phosphoric acid solution and taken up with godet rolls.

The yarn thus obtained was washed until the concentration of phosphoric acid in the yarn became 0.5% by weight and neutralized with an aqueous solution of sodium hydroxide. The yarn was further washed with water and dried at 200° C. The obtained yarn had a strength of 38 g/d, and an elastic modulus of 1034 g/d.

COMPARATIVE EXAMPLE 1

4,6-Diaminoresorcinol dihydrochloride synthesized according to the method described in Japanese Patent Application under PCT laid-open under kohyo No. 500743/1990 was preserved without a reducing agent for 3 months at 30° C. in contact with the air. The decomposition degree was measured and found to be 0.38%. This 4,6-diaminoresorcinol dihydrochloride was polymerized in the same manner as in Example 2. As a result, the obtained polymer dope was green and had an intrinsic viscosity of 18 dl/g.

EXAMPLES 4–7

In the same manner as in Example 1 except that the reducing agents shown in Table 1 were added instead of tin (II) chloride, 4,6-diaminoresorcinol dihydrochlorides were obtained. The obtained DARs were preserved for 3 months at 30° C. in contact with the air. The decomposition degree was measured and found to be 0.31% by weight in each example. The polymer dopes obtained by polymerizing DAR in the same manner as in Example 2 were yellow and had an intrinsic viscosity of 35–48 dl/g.

COMPARISON EXAMPLE 2

In the same manner as in Example 1 except that Pd was added as the reducing agent instead of tin (II) chloride, DAR was obtained. The obtained DAR was preserved for 3 months at 30° C. in contact with the air. The decomposition degree was measured and found to be 0.31% by weight. The polymer dope obtained by polymerization using this DAR in the same manner as in Example 2 was purple and had an intrinsic viscosity of 12 dl/g.

COMPARISON EXAMPLE 3

In the same manner as in Example 1 except that Zn powder upon dispersion in water was added as the reducing agent instead of tin (II) chloride, DAR was obtained. The obtained DAR was preserved for 3 months at 30° C. in contact with the air, and its decomposition degree was measured. The decomposition degree was inconsistent and was 0.02–0.28% by weight and DAR had purple specks. The polymer dope obtained by polymerization using this DAR was yellow-green and had an intrinsic viscosity of 34 dl/g. Hydrogen was generated during polymerization and operation was very difficult.

DAR and PBO obtained in Examples and Comparative Examples above were evaluated, the results of which are shown in the following Table 1.

TABLE 1

|  | Ex. 2 | Ex. 4 | Ex. 5 | Ex. 6 | Ex. 7 | Com. Ex. 1 | Com. Ex. 2 | Com. Ex. 3 |
| --- | --- | --- | --- | --- | --- | --- | --- | --- |
| Reducing Agent | $SnCl_2$ | $TiCl_3$ | CuCl | $H_3PO_3$ | $H_2SO_3$ | none | Pd | Zn |
| Standard redox potential (volt) | 0.15 | 0.04 | 0.153 | −0.20 | 0.17 |  | 0.83 | −0.763 |
| Amount added (ppm) | 2880 | 3860 | 5300 | 5300 | 420 |  | 2400 | 2800 |
| Decomposition degree (%) | 0.0 | 0.0 | 0.0 | 0.0 | 0.0 | 0.38 | 0.31 | 0.02–0.28 |
| Intrinsic viscosity (dl/g) | 38 | 48 | 43 | 44 | 35 | 18 | 12 | 34 |
| Dope color | yellow | yellow | yellow | yellow | yellow | green | purple | yellow |
| Note |  | *1 | *2 |  |  |  |  | *3 |

*1, *2: DAR was colored. *3: Hydrogen was generated during polymerization.

As is evident from Table 1, the present invention improves storage stability of 4,6-diaminoresorcinol. This in turn results in easy handling and long-term preservation. Thus, a high quality polymer PBO can be easily produced and the invention greatly contributes to the industrial field.

Due to the method of the present invention, DAR upon preservation in contact with the air at room temperature for not less than 1 month, or at room temperature under a nitrogen atmosphere for not less than 1 year, does not suffer from degradation caused by oxidation. The PBO obtained therefrom also has superior property of high polymerization degree.

This application is based on application No. 152500/1997 filed in Japan, the content of which is incorporated hereinto by reference.

What is claimed is:

1. A composition consisting essentially of 4,6-diaminoresorcinol or a salt thereof, and a reducing agent having a standard redox potential of not less than −0.20 volt and not more than 0.34 volt, the reducing agent being contained in a proportion of not less than 100 ppm and not more than 10,000 ppm of 4,6-diaminoresorcinol.

2. A method for producing polybenzbisoxazole, comprising reacting 4,6-diamino-resorcinol or a salt thereof with an aromatic dicarboxylic acid in the presence of a reducing agent having a standard redox potential of not less than −0.20 volt and not more than 0.34 volt, in a proportion of not less than 100 ppm and not more than 10,000 ppm of 4,6-diaminoresorcinol.

3. A method for stabilizing 4,6-diaminoresorcinol or a salt thereof during storage, comprising storing 4,6-diaminoresorcinol or salt thereof in the presence of a reducing agent having a standard redox potential of not less than −0.20 volt and not more than 0.34 volt, in a proportion of not less than 100 ppm and not more than 10,000 ppm of 4,6-diaminoresorcinol.

* * * * *

UNITED STATES PATENT AND TRADEMARK OFFICE

CERTIFICATE OF CORRECTION

PATENT NO. : 5,911,908

DATED : June 10, 1998

INVENTOR(S) : Go MATSUOKA and Fuyuhiko KUBOTA

It is certified that error appears in the above-identified patent and that said Letters Patent is hereby corrected as shown below:

```
Title page
```
Insert at [30] Foreign Application Priority Data
    Oct. 6, 1997    [JP]  Japan         9-152500

Signed and Sealed this

Twenty-third Day of May, 2000

Attest:

Q. TODD DICKINSON

*Attesting Officer*      *Director of Patents and Trademarks*

UNITED STATES PATENT AND TRADEMARK OFFICE
CERTIFICATE OF CORRECTION

PATENT NO. : 5,911,908

ISSUED : June 15, 1999

INVENTOR(S) : Go MATSUOKA and Fuyuhiko KUBOTA

It is certified that error appears in the above-identified patent and that said Letters Patent is hereby corrected as shown below:

On the title page,

In [30] Foreign Application Priority Data
"Oct. 6, 1997" should read --Jun. 10, 1997--.

Signed and Sealed this

Thirteenth Day of March, 2001

Attest:

NICHOLAS P. GODICI

Attesting Officer

Acting Director of the United States Patent and Trademark Office